United States Patent
Oh et al.

(10) Patent No.: US 7,172,996 B2
(45) Date of Patent: Feb. 6, 2007

(54) CLEANING AGENT COMPOSITION FOR A POSITIVE OR A NEGATIVE PHOTORESIST

(75) Inventors: Sae-Tae Oh, Pyongtaek (KR); Doek-Man Kang, Seocho-gu (KR); Kyung-Soo Choi, Daejon (KR)

(73) Assignee: Az Electronic Materials USA Corp., Somerville, NJ (US)

( * ) Notice: Subject to any disclaimer, the term of this patent is extended or adjusted under 35 U.S.C. 154(b) by 399 days.

(21) Appl. No.: 10/500,752

(22) PCT Filed: Jan. 9, 2003

(86) PCT No.: PCT/KR03/00030

§ 371 (c)(1),
(2), (4) Date: Jul. 1, 2004

(87) PCT Pub. No.: WO03/058350

PCT Pub. Date: Jul. 17, 2003

(65) Prior Publication Data

US 2005/0119142 A1    Jun. 2, 2005

(30) Foreign Application Priority Data

Jan. 11, 2002  (KR) ............... 10-2002-0001773
Sep. 4, 2002   (KR) ............... 10-2002-0053240

(51) Int. Cl.
C11D 7/50 (2006.01)

(52) U.S. Cl. ............... 510/175; 510/176; 510/365

(58) Field of Classification Search ............. None
See application file for complete search history.

(56) References Cited

U.S. PATENT DOCUMENTS

| | | | |
|---|---|---|---|
| 3,666,473 A | 5/1972 | Colom et al. | |
| 4,115,128 A | 9/1978 | Kita | |
| 4,165,295 A * | 8/1979 | Vander Mey | 510/176 |
| 4,173,470 A | 11/1979 | Fahrenholtz et al. | |
| 4,215,005 A * | 7/1980 | Vander Mey | 510/176 |
| 4,221,674 A * | 9/1980 | Vander Mey | 510/176 |

(Continued)

FOREIGN PATENT DOCUMENTS

EP    0 065 381 A2    11/1982

(Continued)

Primary Examiner—Gregory Webb
(74) Attorney, Agent, or Firm—Sangya Jain

(57) ABSTRACT

The present invention relates to a composition for cleaning a photoresist and is to provide a cleaning composition wherein the residue of the photoresist does not remain on the boundary surface between the cleaned area and the not-cleaned area after a negative photoresist containing pigment is cleaned, soft-baked, exposed and developed. The present invention provides a composition for cleaning a positive or negative photoresist which comprises (a) from 0.1 to 20 wt. % of and alkyl oxide polymer with a molecular weight of from 50 to 2000 and (b) from 80 to 99.9 wt. % of an organic solvent comprising: (b–1) from 1 to 20 parts by weight of dipropylene glycol methyl ether (DPGME), from 10 to 50 parts by weight of N-methyl pyrolidone (NMP) and from 50 to 90 parts by weight of methyl isobutyl ketone (MIBK), or (b–2) from 10 to 90 parts by weight of dimethyl formaldehyde (DMF) or dimethylacetamide (DMAc) and from 10 to 50 parts by weight of n-butyl acetate.

9 Claims, 1 Drawing Sheet

Composition of comparative example 1

Composition of examples 1 and 2

* X axis: Distance from the cleaned area (unit: 1nm).

* Y axis: Height of the photoresist coating (unit: 0.1μm).

U.S. PATENT DOCUMENTS

| | | | |
|---|---|---|---|
| 4,395,348 A * | 7/1983 | Lee | 510/176 |
| 4,403,029 A * | 9/1983 | Ward et al. | 510/176 |
| 4,749,510 A | 6/1988 | Nelson | |
| 5,098,591 A | 3/1992 | Stevens | |
| 5,288,335 A | 2/1994 | Stevens | |
| 5,346,640 A * | 9/1994 | Leys | 510/174 |
| 5,472,830 A * | 12/1995 | Honda | 510/176 |
| 5,507,978 A * | 4/1996 | Honda | 510/176 |
| 5,545,353 A * | 8/1996 | Honda et al. | 510/176 |
| 5,554,312 A * | 9/1996 | Ward | 510/175 |
| 5,561,105 A * | 10/1996 | Honda | 510/178 |
| 5,597,678 A * | 1/1997 | Honda et al. | 430/331 |
| 5,612,303 A * | 3/1997 | Takayanagi et al. | 510/174 |
| 5,612,304 A * | 3/1997 | Honda et al. | 510/176 |
| 5,962,383 A * | 10/1999 | Doyel et al. | 510/164 |
| 5,988,186 A * | 11/1999 | Ward et al. | 134/1.3 |
| 6,017,862 A * | 1/2000 | Doyel et al. | 510/163 |
| 6,060,439 A * | 5/2000 | Doyel et al. | 510/164 |
| 6,130,195 A * | 10/2000 | Doyel et al. | 510/365 |
| 6,323,169 B1 * | 11/2001 | Abe et al. | 510/176 |
| 6,368,421 B1 * | 4/2002 | Oberlander et al. | 134/40 |
| 6,531,436 B1 * | 3/2003 | Sahbari et al. | 510/176 |

FOREIGN PATENT DOCUMENTS

| | | |
|---|---|---|
| EP | 0 376 687 | 7/1990 |
| WO | WO 03/058350 A1 | 7/2003 |

* cited by examiner

[Figure-1]
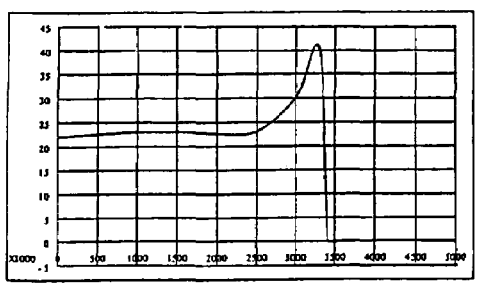 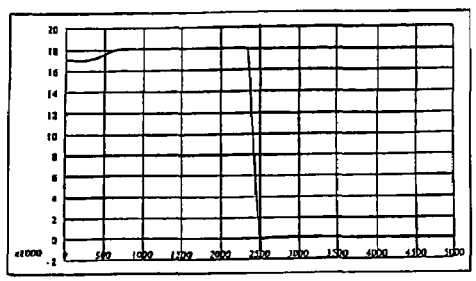
Composition of comparative example 1    Composition of examples 1 and 2
* X axis: Distance from the cleaned area (unit: 1nm).
* Y axis: Height of the photoresist coating (unit: 0.1μm).
[Figure-2]
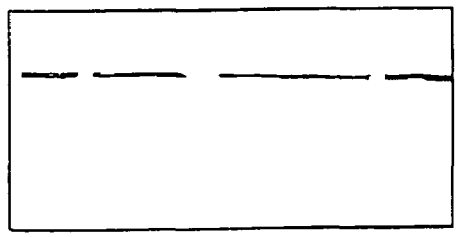 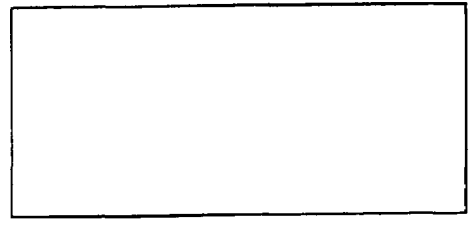
Composition of comparative example 1    Composition of examples 1 and 2

CLEANING AGENT COMPOSITION FOR A POSITIVE OR A NEGATIVE PHOTORESIST

TECHNICAL FIELD

The present invention relates to a composition for cleaning a photoresist and, more specifically, to a composition for cleaning a photoresist which is useful for removing photosensitive material remaining on undesirable areas of the substrate for coating a photosensitive material and the instrument contacting the photosensitive material during processing of a fine circuit using a positive or negative photoresist composition and a negative photoresist composition containing pigment.

BACKGROUND ART

It is well known in the art to produce photoresist compositions such as those described in U.S. Pat. Nos. 3,666,473, 4,115,128 and 4,173,470. These include phenol-formaldehyde novolak resins together with light-sensitive materials, usually a substituted naphthoquinone diazo compound.

The novolak resin component of those photoresist compositions is soluble in an alkaline aqueous solution, but the naphthoquinone diazo compound acts as a dissolution rate inhibitor with respect to the resin. Upon exposure of selected areas of the coated substrate to actinic radiation, however, the photoresist undergoes a radiation induced structural transformation and the exposed areas of the coating are rendered more soluble than the unexposed areas. The relief pattern of photoresist on substrate prepared by the process mentioned above is useful for providing 1 µm very small line and space widths, for example, in the manufacture of a semiconductor.

Further, in the process for preparing such very small circuits, the circuit density can be increased, using photolithography techniques, by increasing the resolution capabilities of the resist. Such photoresist has been widely used for preparing a semiconductor and a liquid crystal display device. In the liquid crystal display device, examples of using a photosensitive material during color filter process are described in more detail below.

In the color filter process, a positive photosensitive material or a negative photosensitive material containing pigment was coated on the glass or conductive metal film or layer having a rectangular pattern (hereinafter referred to as "substrate"), soft-baked, exposed and developed to prepare a pattern of the desired shape. In the course of forming such fine circuit pattern, when forming a photosensitive film on the substrate, the photoresist film formed at the edge of the substrate becomes irregular when compared with the photoresist film formed at the middle of the substrate. Further, the photosensitive material coated irregularly at the edge of the substrate during soft-baking or exposing process may lead to contamination by an accumulation of photosensitive material and thus, the removal thereof is required.

As the process for removing the coated photoresist layer by a physical process, a process for scraping the layer is known. However, such process has a problem in that the removal of the layer is not regular and the layer is damaged. As the process for stripping and cleaning the photoresist layer by a chemical process, the process for removing the photoresist layer with a chemical solution is known.

U.S. Pat. No. 4,983,490 discloses a solution for treating a photoresist film which comprises from 1 to 10 parts by weight of propylene glycol alkylether (PGME) and from 1 to 10 parts by weight of propylene glycol alkyl ether acetate (PGMEA), which exhibits excellent properties mainly in treating a positive photoresist, but it has disadvantages in treating a negative photoresist. The negative photoresist containing pigment is a photoresist used for a color filter of liquid crystal display devices. As such photoresist, black, red, blue and green photoresists may be used. When the photoresist containing pigment is cleaned with the cleaning composition consisting of from 1 to 10 parts by weight of PGME and from 1 to 10 parts by weight of PGMEA, the cleaning capability is lowered and a residue of the photoresist remains on the boundary surface between the cleaned area and the not-cleaned area of the developer after developing process.

DISCLOSURE OF INVENTION

The purpose of the present invention is to provide a cleaning composition wherein the residue of the photoresist does not remain on the boundary surface between the cleaned area and the not-cleaned area after a negative photoresist containing pigment is cleaned, soft-baked, exposed and developed.

Another purpose of the present invention is to provide a cleaning composition which does not produce a build-up property where the photoresist layer raises higher than the original coated thickness on the boundary surface between the area cleaned by the cleaning composition and the area not cleaned.

The further purpose of the present invention is to provide a photoresist layer cleaning composition that has an excellent cleaning property.

In order to accomplish the purposes mentioned above, the present invention provides a cleaning composition which comprises (a) from 0.1 to 20 wt. % of an alkyl oxide polymer with a molecular weight of from 50 to 2000 and (b) from 80 to 99.9 wt. % of an organic solvent.

The organic solvent (b) preferably includes (b–1) a mixture of methyl isobutyl ketone (MIBK), dipropylene glycol methyl ether(DPGME) and N-methyl pyrolidone(NMP), or (b–2) a mixture of dimethyl formamide(DMF) and n-butyl acetate, or (b–3) a mixture of dimethylacetamid(DMAc) and n-butyl acetate. Hereinafter, the present invention is described in detail.

The cleaning composition of the present invention comprises (a) an alkyl oxide polymer with a molecular weight of from 50 to 2000; and (b) organic solvent which contains (b–1) a mixture of methyl isobutyl ketone (MIBK), dipropylene glycol methyl ether(DPGME) and N-methyl pyrolidone(NMP), or (b–2) a mixture of dimethyl formamide (DMF) and n-butyl acetate, or (b–3) a mixture of dimethylacetamide(DMAc) and n-butyl acetate.

The preferred amount of the alkyl oxide polymer(a) is from 0.1 to 20 wt. % with respect to the total amount of the composition. When the amount of the polymer exceeds 20 wt. %, it is not completely volatilized during soft-bake and thus, it is not preferable. When the amount is less than from 0.1 wt. %, the residual photosensitive material remains on the boundary surface between the cleaned area and the not-cleaned area after the coated photosensitive material is exposed to light and developed.

Further, even when the molecular weight of the polymer exceeds 2000, there is a problem in that it is not completely volatilized. When the molecular weight is less than 500, the residual photosensitive material remains on the boundary surface between the cleaned area and the not-cleaned area after the coated photosensitive material is exposed to light and developed. This is not preferable.

The most preferable alkyl oxide polymer is an ethylene or propylene oxide polymer, and even if any group is substituted on the two end groups of the alkyl oxide polymer, the performance does not change. The compositions of the organic solvent (b) suitable for mixing with the alkyl oxide polymer (a) are as follows:

(b–1) One example of the preferred organic solvent mixture is a mixture consisting of from 1 to 20 parts by weight of dipropylene glycol methyl ether (DPGME), from 10 to 50 parts by weight of N-methyl pyrolidone (NMP) and 50 to 90 parts by weight of methyl isobutyl ketone (MIBK).

In the case of dipropylene glycol methyl ether (DPGME), when exceeding 20 parts by weight, it is not completely volatilized and thus it is not preferable. When the amount is less than 1 part by weight, the cleaning power is lowered and thus it is not preferable. In the case of the N-methyl pyrolidone(NMP), when it is mixed in the amount of less than 10 parts by weight, the cleaning power is abruptly lowered and thus it is not preferable. Therefore, it is particularly preferable to mix NMP in the amount of up to 50 parts by weight. In the case of the methyl isobutyl ketone (MIBK), when it is mixed in the amount of less than 50 parts by weight, the cleaning power is lowered and thus it is not preferable. It is particularly preferable to mix MIBK in the amount of up to 90 parts by weight.

(b–2) The second example of the preferred organic solvent mixture is a mixture consisting of from 10 to 90 parts by weight of dimethyl formamide (DMF) and from 10 to 50 parts by weight of n-butyl acetate. When the amount of n-butyl acetate exceeds 50 parts by weight or is less than 10 parts by weight, there is a problem that the cleaning power is lowered.

(b–3) Another preferred organic solvent mixture is a mixture consisting of from 10 to 90 parts by weight of dimethylacetamide(DMAc) and from 10 to 50 parts by weight of n-butyl acetate. When the amount of n-butyl acetate exceeds 50 parts by weight or is less than 10 parts by weight, there is a problem that the cleaning power is lowered.

In case of the organic solvent (b–1), (b–2), and (b–3), the excellent property of not producing a build-up property where the coating thickness of the photoresist becomes thicker than the original coated thickness, upon cleaning of a positive photoresist, on the boundary surface between the cleaned area and the not-cleaned area of the photosensitive materials is achieved.

BRIEF DESCRIPTION OF DRAWINGS

FIG. 1 is a graph showing respective build-up properties when positive photoresist was cleaned with the cleaning composition of the present invention and with the cleaning agent of a conventional organic solvent.

FIG. 2 shows a residual of photoresist when a color photoresist was cleaned with the cleaning composition of the present invention.

Hereinafter, the present invention is more specifically described by way of examples and comparative examples.

EXAMPLE 1

The positive photoresist, AZ HKT501, was coated on a 370 mm×470 mm glass substrate using a spinner. The photoresist layer was dissolved and removed from the peripheral area and the back area of the glass plate using a composition prepared by mixing 3 wt. % of alkyl oxide polymer having molecular weight of 300 with an organic solvent of 80 wt. % of DMF or DMAc and 17 wt. % of n-butyl acetate in DNS EBR apparatus. The results were observed by microscope and confirmed that no residual photoresist remained.

EXAMPLE 2

The photoresist layer was dissolved and removed from the peripheral area and the back area of the glass plate using, as a removing solvent cleaning composition, a composition prepared by mixing 3 wt. % of alkyl oxide polymer having molecular weight of 300 with an organic solvent of 7 wt. % of DPGME, 20 wt. % of NMP and 70 wt. % of MIBK, instead of the solvent of Example 1. The results were observed by microscope and confirmed that no residual photoresist remained.

COMPARATIVE EXAMPLE 1

An experiment was conducted in the same manner as Example 1 using, as the removing solvent, 30 wt. % of propylene glycol monomethyl ether acetate (PGMEA) and 70 wt. % of propylene glycol monomethyl ether(PGME). The build up was measured and the result is shown in FIG. 1.

FIG. 1 is a graph showing build up properties when the substrate is coated with the cleaning composition of the present invention prepared in Examples 1 and 2 and with the cleaning composition using the general organic solvent in Comparative Example 1, after the positive photoresist AZ HKT501 is coated on the substrate. As shown in FIG. 2, the residual photosensitive material remains on the boundary surface between the cleaned area and the not-cleaned area after the coated photosensitive material is exposed to light and developed.

FIG. 2 is a photograph showing a residual of the photoresist when a color photosensitive agent is cleaned with the cleaning composition of the present invention prepared in Example 1 and 2. As shown in FIG. 2, JSR color photoresists (R, G, B) were coated on the substrate, washed with the cleaning composition of the present invention prepared in Examples 1 and 2, baked and developed. As a result, it can be confirmed that no residue of the photoresist remained.

Effect of Invention

As set forth above, the composition for cleaning the positive or negative photoresist has an excellent washing power since no residue remains after cleaning. The build up phenomenon is not produced on the boundary surface between the cleaned area and the not-cleaned area. There is no problem that the cleaning solution is immersed into the photoresist to change the coating thickness.

The invention claimed is:

1. A composition for cleaning a positive or negative photoresist which comprises (a) from 0.1 to 20 wt. % of an alkyl oxide polymer with a molecular weight of from 50 to 2000; and (b) from 80 to 99.9 wt. % of an organic solvent containing from 1 to 20 parts by weight of dipropylene glycol alkyl ether (DPGAE), from 10 to 50 parts by weight of N-methyl pyrolidone (NMP) and from 50 to 90 parts by weight of methyl isobutyl ketone (MIBK).

2. The composition for cleaning a positive or negative photosensitive material of claim 1, wherein the alkyl oxide polymer is ethylene oxide polymer.

3. The composition for cleaning a positive or negative photosensitive material of claim 1, wherein the alkyl oxide polymer is propylene oxide polymer.

4. The composition for cleaning a positive or negative photosensitive material of claim 1, wherein the dipropylene glycol alkylether is dipropylene glycol methyl ether.

5. A composition for cleaning a positive or negative photoresist which comprises (a) from 0.1 to 20 wt. % of an alkyl oxide polymer with a molecular weight of from 50 to 2000 ; and (b) from 80 to 99.9 wt. % of an organic solvent containing from 10 to 90 parts by weight of dimethyl formamide (DMF) ordimethylacetamide(DMAc) and from 10 to 50 parts by weight of n-butyl acetate.

6. The composition for cleaning a positive or negative photosensitive material of claim 5, wherein the alkyl oxide polymer is ethylene oxide polymer.

7. The composition for cleaning a positive or negative photosensitive material of claim 5, wherein the alkyl oxide polymer is propylene oxide polymer.

8. A process for cleaning a positive or negative photoresist which comprises,
   a) forming a coating of the photoresist on a substrate; and,
   b) removing the photoresist from peripheral area using the composition from claim 1.

9. A process for cleaning a positive or negative photoresist which comprises,
   a) forming a coating of the photoresist on a substrate; and,
   b) removing the photoresist from peripheral area using the composition from claim 5.

* * * * *